(12) United States Patent
Bertsch et al.

(10) Patent No.: US 8,302,376 B2
(45) Date of Patent: Nov. 6, 2012

(54) FIBER STRAND AND IMPLANTABLE SUPPORTING BODY HAVING A FIBER STRAND

(75) Inventors: Torben Bertsch, Nürnberg (DE); Heinz Müller, Erlangen (DE)

(73) Assignee: Biotronik VI Patent AG, Baar (CH)

( * ) Notice: Subject to any disclaimer, the term of this patent is extended or adjusted under 35 U.S.C. 154(b) by 0 days.

(21) Appl. No.: 13/205,871

(22) Filed: Aug. 9, 2011

(65) Prior Publication Data

US 2011/0293936 A1 Dec. 1, 2011

Related U.S. Application Data

(63) Continuation of application No. 12/480,683, filed on Jun. 9, 2009, now Pat. No. 7,997,054.

(30) Foreign Application Priority Data

Jun. 25, 2008 (DE) .......................... 10 2008 002 641

(51) Int. Cl.
*D02G 3/36* (2006.01)
(52) U.S. Cl. ......................................................... 57/257
(58) Field of Classification Search ................... 57/209, 57/252, 255, 256, 257, 258
See application file for complete search history.

(56) References Cited

U.S. PATENT DOCUMENTS

| | | | | |
|---|---|---|---|---|
| 4,084,399 A * | 4/1978 | Kanemaru et al. | | 57/232 |
| 4,144,702 A * | 3/1979 | Pittman | | 57/409 |
| 4,144,703 A * | 3/1979 | Ingham, Jr. | | 57/409 |
| 4,160,359 A * | 7/1979 | Frentress | | 57/409 |
| 4,218,868 A * | 8/1980 | Pittman | | 57/209 |
| 4,383,403 A * | 5/1983 | Nakayama et al. | | 57/207 |
| 4,520,623 A * | 6/1985 | Ogawa et al. | | 57/236 |
| 5,591,199 A * | 1/1997 | Porter et al. | | 623/1.21 |
| 6,032,450 A * | 3/2000 | Blum | | 57/75 |
| 6,500,203 B1 * | 12/2002 | Thompson et al. | | 623/1.13 |
| 6,585,758 B1 * | 7/2003 | Chouinard et al. | | 623/1.16 |
| 6,994,723 B1 * | 2/2006 | McMahon | | 623/1.49 |
| 7,997,054 B2 * | 8/2011 | Bertsch et al. | | 57/257 |
| 2004/0138644 A1 | 7/2004 | DiCarlo et al. | | |
| 2005/0283220 A1 | 12/2005 | Gobran et al. | | |
| 2005/0288775 A1 | 12/2005 | Dong | | |
| 2006/0212127 A1 | 9/2006 | Karabey et al. | | |
| 2006/0276887 A1 * | 12/2006 | Brady et al. | | 623/1.53 |
| 2007/0207186 A1 | 9/2007 | Scanlon et al. | | |

FOREIGN PATENT DOCUMENTS

| | | |
|---|---|---|
| DE | 69627658 T2 | 4/2004 |
| EP | 1 258 229 A1 | 11/2002 |
| WO | 00/44308 A2 | 8/2000 |

* cited by examiner

*Primary Examiner* — Shaun R Hurley
(74) *Attorney, Agent, or Firm* — Biotech Beach Law Group PC

(57) ABSTRACT

The invention relates to a fiber strand (10) for an implantable supporting body (100) comprising at least two individual fibers (12). The at least two individual fibers (12) are each shorter in their longitudinal extent than the longitudinal extent (14) of the fiber strand, and in their transverse extent they are each thinner than the transverse extent (16) of the fiber strand.

20 Claims, 4 Drawing Sheets

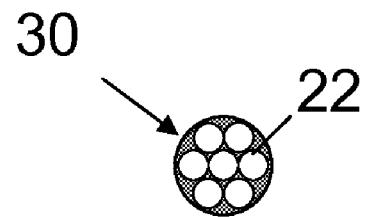
FIG. 3a  FIG. 3b
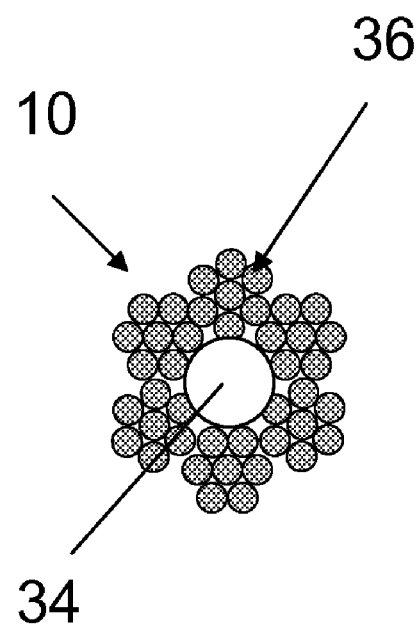
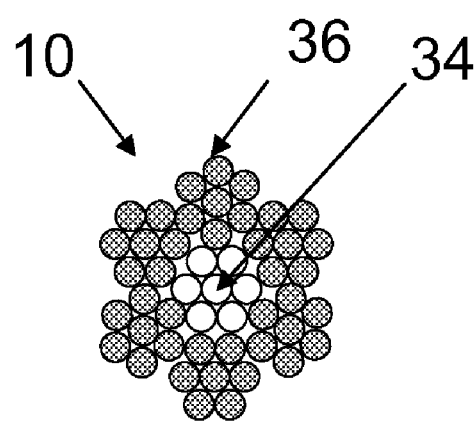
FIG. 3c  FIG. 3d

FIBER STRAND AND IMPLANTABLE SUPPORTING BODY HAVING A FIBER STRAND

CROSS REFERENCE TO RELATED APPLICATIONS

This application is a continuation of U.S. patent application Ser. No. 12/480,683, filed Jun. 9, 2009, which claims benefit of priority to German patent application number DE 10 2008 002 641.7, filed on Jun. 25, 2008; the contents of each are incorporated herein by reference in their entirety.

TECHNICAL FIELD

The invention relates to a fiber strand and an implantable supporting body having a fiber strand including at least two fibers that are each shorter in their longitudinal extent than the longitudinal extent of the fiber strand.

BACKGROUND OF THE INVENTION

Today's implantable supporting bodies, so-called stents, are limited with regard to their mechanical possibilities. For example, no structures representing the physiological needs of the surrounding tissue have been implementable according to the previous methods. Radial or longitudinal forces or forces occurring differently in sections of the implant could in the past be imitated and simulated only individually by an implant but not as a totality, which is why the function and compatibility of such implants are limited.

The purpose of many endoprostheses is to assume a supporting function inside a patient's body. Accordingly, endoprostheses are designed to be implantable and have a supporting structure, which guarantees the supporting function. Implants made of solid metallic structures are known. The choice of metals as the material for the supporting structure of such an implant is based on empirical values from classical mechanics and their relatively well-controlled biocompatibility.

Metallic stents are known in large numbers and in various embodiments. For example, US 2006/0212055 A1 discloses various embodiments of stents comprising individual fibers, for example. One of the main areas of application of such stents is for permanent dilatation of vascular occlusions, in particular stenoses of the coronary vessels and for maintaining their patency. Through the use of stents, the optimum vascular cross section required for primary therapeutic success can be achieved, but the permanent presence of such a foreign body initiates a cascade of microbiological processes, which may lead to a gradual occlusion of the stent.

BRIEF SUMMARY OF THE INVENTION

The object of the invention is to create a fiber strand and an implantable supporting body having a fiber strand to improve upon the problems associated with the state of the art. Likewise, a method for manufacturing a supporting body is also to be provided.

This object is achieved according to the present invention by the features of the independent claims. Advantageous embodiments and advantages of the invention are derived from the additional claims and the description.

The invention is directed to a fiber strand comprising at least two individual fibers. It is proposed that the at least two individual fibers shall each be shorter in the longitudinal extent of each individual fiber than the longitudinal extent of the fiber strand and that the transverse extent of the individual fibers shall be thinner than the transverse extent of the fiber strand in a product formed from the fiber strand in the individual case. A fiber strand having readily controllable and predictable properties can be produced through a suitable choice of materials and through a selected processing density. Depending on the processing density, the fiber strand may be designed to be more or less flexible, have more or less mechanical strength, be more or less low-stretch and/or more or less hard. The mechanical properties may also be characterized differently in different directions. Depending on the composition of the fiber strand, the chemical stability may be adjusted in a targeted manner. Erosion and medication, if desired, may be adjusted in a targeted manner by means of different fiber structures and/or their composition. The longitudinal and transverse extents of the fiber strand are preferably understood to be the dimensions, which correspond to the longitudinal and transverse extent of the fiber strand in this product in the event of further processing to a preferred implantable supporting body and/or to a preferred supporting structure. A fiber body may be formed from the fiber strand by reshaping the fiber strand or by joining more than one fiber strand, preferably at least two fiber strands.

It is advantageously possible to create a controllable and individually adjustable supporting structure.

The ratio of the longitudinal extent of the individual fiber to the fiber strand longitudinal extent may preferably be in the range between 2:1 and 200,000:1, especially between 10:1 and 100,000:1. The ratio of the transverse extent of the individual fiber to the transverse extent of the fiber strand may preferably be in the range between 2:1 and 200,000:1, preferably between 10:1 and 100,000:1. The ratio of the longitudinal extent may be unrelated to the ratio of the transverse extent. Due to the preferably very short lengths and/or diameters of the individual fibers in comparison with the dimensions of a preferred supporting body formed from the fiber strand, the desired mechanical properties can be adjusted especially easily. In addition, a wide variety of materials can be combined. A large surface area can be created to accommodate drugs in the fiber strand. To have positive medical effects locally and/or regionally, a biologically active substance and/or material may also be introduced in fiber form to induce local and/or regional medically positive effects.

According to an advantageous embodiment, at least one of the individual fibers may comprise a material from the group of carbon and carbonaceous material. In particular carbon fibers may be used, polymers or organic or semiorganic materials. Semiorganic materials are materials that originate from organisms that were alive at one time or structures based on them.

According to another advantageous embodiment, at least one of the individual fibers may be formed from a metallic material comprising at least one member/element from the group of Fe, Cr, Co, Wo, Ni, Zn, Mg, Ti, Mn, Pt, Mo, Ta, Ir, Ag, Au in crystalline, partially crystalline and/or amorphous structure. Pure materials and/or alloys and/or compounds of one or more of the members of the group may be provided. The individual fibers may consist of an amorphous metal and/or alloy, e.g., metallic glasses, for example.

According to another advantageous embodiment, at least one of the individual fibers may be formed from at least one ceramic material comprising at least one member/element from the group of Br, I, Zr, Al, N, F, Si, Ga, Ti, O, Au, Ag in crystalline, partially crystalline and/or amorphous structure. Pure materials and/or alloys and/or compounds of one or more of the members of the group may be provided.

Likewise, an embodiment comprising a mixture of individual fibers selected from at least two of the aforementioned groups may also be possible. A wide variety of materials may thus be combined easily in the form of individual fibers. The fiber strand formed in this way can be optimized accordingly through a suitable combination of individual fibers having desired properties.

Parts of this blend and/or combination of individual fibers may already consist of medically active materials and/or medically active substances may be incorporated into individual fibers and/or remodeling products or degradation products may achieve positive medical effects.

The fiber strand may be impregnated with a matrix material, which may surround the individual fibers. The matrix material may preferably comprise at least one substance from the group of drugs, polymers, drug-loaded polymers, drug-loaded biodegradable and/or bioresorbable polymers, in particular at least one substance from the group of lipid regulators (fibrates), immunosuppressants, vasodilators (sartans), calcium channel blockers, calcineurin inhibitors (tacrolimus), antiphlogistics (cortisone, diclofenac), anti-inflammatories (imidazoles), anti-allergics, oligo-nucleotides (dODN), estrogens (genistein), endothelializing agents (fibrin), steroids, proteins/peptides, prolif-eration inhibitors, analgesics and antirheumatics, paclitaxel, rapamycin, loaded polymers, nonresorbable permanent polymers such as polypropylene, polyethylene, polyvinyl chloride, polyacrylates (polyethyl acrylate and polymethyl acrylate, polymethyl methacrylate, polymethyl-co-ethyl acrylate, ethylene/ethyl acrylate), poly-tetrafluoroethylene (ethylene/chlorotrifluoroethylene copolymer, ethylene/tetrafluoroethylene copolymer), poly-amides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, silicones, poly-phosphazene, polymer foams (e.g., from carbonates, styrenes) as well as the copolymers and blends of the classes listed and/or the class of thermoplastics and elastomers in general and/or polymers loaded with resorbable/bioresorbable/degradable polymers such as polydioxanone, polyglycolide, polycaprolactone, polylactides [poly-L-lactide, poly-D,L-lactide and copolymers as well as blends such as poly(L-lactide-co-glycolide), poly(D,L-lactide-co-glycolide), poly(L-lactide-co-D,L-lactide), poly(L-lactide-co-trimethylene carbonate)], triblock copolymers, polysaccharides [chitosan, levan, hyaluronic acid, heparin, dextran, cellulose, etc.), polyhydroxy-valerate, ethylvinyl acetate, polyethylene oxide, poly-phosphorylcholine, fibrin, albumin, polyhydroxybutyric acid (atactic, isotactic, syndiotactic and blends thereof), etc.

One or more drugs can be incorporated into a local, regional and/or systemic treatment by means of a product formed from the fiber strand by using carrier substances. Suitable carrier substances include degradable or nondegradable polymers, fats or other organic compounds, e.g., sugars, proteins, etc. One or more drugs may also be incorporated directly in the form of coatings or through the use of cavities, e.g., between the individual fibers. Depending on the fiber composition, the chemical stability may be adjusted in various ways in the form of erosion. The polymer may advantageously be formed from at least one monomer from the group of lactides, glycolides, paradioxanone, caprolactone, trimethylene carbonate, blends thereof and copolymers thereof. These are preferably biodegradable substances, so that a biodegradable product, e.g., an implantable supporting body, can be produced from the fiber strand.

The individual fibers may preferably be twisted, braided and/or woven to form the fiber strand. They thus form an intimate bond with a surface area of an adjustable size. The mechanical properties of the fiber strand can be adjusted, depending on the type of mechanical bond and the individual fiber material.

The fiber strand may advantageously be processed to form a fiber body in a three-dimensional shape, e.g., a tube, or in a flat shape, e.g., a sheet, or as a ribbon, e.g., as a cord. The fiber body embodied as a cord may comprise one or more cords; likewise, the fiber body may be formed of multiple fiber strands or cords or the fiber strand is formed directly as a band or tube.

A fiber body formed as a tube may advantageously form the load-bearing structure of an implantable supporting body. Alternatively, the load-bearing structure of a preferred implantable supporting body may be formed from a suitable combination of at least two cords. Different cords with a different composition of their individual fibers, different drug loading or none at all and/or different mechanical embodiments may be joined together.

According to a preferred embodiment, the fiber strand may be formed so that a sheath comprising one or more cords is arranged around a core. The core may be formed from one or more cords. The sheath may be formed from a material having at least one core enclosed by a sheath. The sheath and/or core may also be formed from cord.

The individual fibers of the fiber strand can be joined together mechanically, e.g., by braiding, weaving, knotting, twisting and the like. Further processing of the fiber strand to a fiber body can be facilitated in this way. The fiber body, embodied as a tube, mat or the like in particular, may be cut to size with predetermined dimensions as desired.

The fiber body embodied as a cord may be treated with a matrix material, if necessary. This may also take place after formation of the cord or in the production of the fiber strands. It is likewise conceivable for impregnated cords to be further processed, e.g., to form another cord and for the finished cord to also be treated with a matrix material. The matrix material for the fiber strand and/or the fiber body formed from the fiber strand and/or the cord may comprise at least one substance from the group of drugs, polymers, drug-loaded polymers, drug-loaded biodegradable polymers. The polymer may be formed from at least one monomer from the group of lactides, glycolides, paradioxanone, caprolactone, trimethylene carbonate, mix-tures thereof, copolymers thereof.

Preferred polymers for the polymer matrix of the inventive implant are selected in particular from the group:

nonresorbable/permanent polymers:
polypropylene, polyethylene, polyvinyl chloride, polymethyl methacrylate, polymethyl methacrylate, polytetrafluoro-ethylene, polyvinyl alcohol, polyurethane, polybutylene terephthalate, silicones, polyphosphazenes, as well as their copolymers and blends;

resorbable/bioresorbable/degradable polymers:
polydioxanone, polyglycolide, polycaprolactone, polylactides (poly-L-lactide, poly-D,L-lactide and copolymers as well as blends, e.g., poly(L-lactide-co-glycolide), poly(D,L-lactide-co-glycolide), poly(L-lactide-co-D,L-lact-ide), poly(L-lactide-co-trimethylene carbonate, triblock copolymers), polysaccharides (chitosan, levan, hyaluronic acid, heparin, dextran, cellulose, etc.), polyhydroxy-valerate, ethylvinyl acetate, polyethylene oxide, polyphosphorylcholine, fibrin, albumin.

The cord may be treated by impregnation or sheathing, e.g., by spraying, dipping and the like in the case of the fiber strand and/or the fiber body, for example.

According to another aspect of the invention an implantable supporting body having a fiber strand with at least one of the features described above is proposed. The mechanical and chemical properties of the supporting body can be adjusted in a targeted manner. The mechanical properties can be characterized differently in different directions through the use of the preferred fiber strand, e.g., in the form of a tube or strand. Depending on the composition of the fiber strand, the stability of the supporting body with respect to chemical attacks can be adjusted in a targeted manner. Erosion and medication, if desired, can be adjusted in a targeted manner through different cords or through compositions of one or more drugs that vary within one cord.

According to another aspect of the invention, a method for manufacturing an implantable supporting body is proposed in which the following steps are performed:

providing a cord and/or a fiber strand, and
cutting the cord and/or the fiber strand to size,
shaping the cord and/or the fiber strand after cutting,
twisting, braiding or weaving the components listed above together to form the final geometry.

The cord and/or fiber strand can be cut to size by means of laser cutting, water jet cutting or other suitable means.

The cord and/or the fiber strand may advantageously be treated with by a matrix material. This may be accomplished by impregnating and/or sheathing, e.g., by means of spraying, dipping and the like.

The cord and fiber strand may be shaped and/or processed further to a desired final geometry after being cut.

BRIEF DESCRIPTION OF THE DRAWINGS

FIGS. 3a-d show various views of components of a fiber strand having a core and a sheath.

BRIEF DESCRIPTION OF THE PREFERRED EMBODIMENT

Figure 1A:
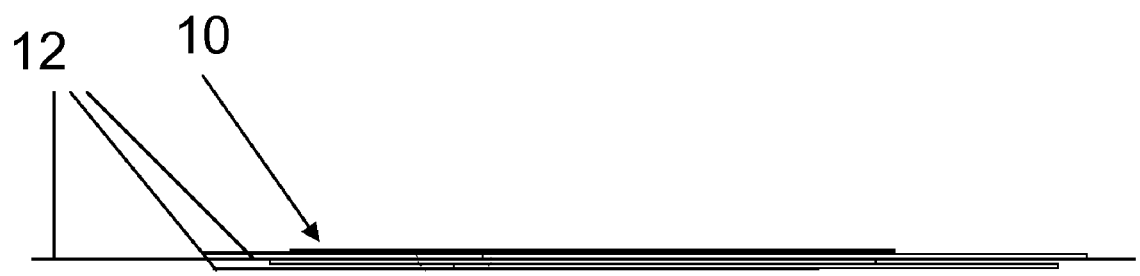
FIGS. 1a-c show an overhead view of a preferred strip-like fiber strand (FIG. 1a) illustrating individual fibers of the fiber strand (FIG. 1b) as well as a detail of a fiber strand.

The invention is explained in greater detail below as an example on the basis of exemplary embodiments illustrated in the drawings in schematic diagrams.

Elements that are functionally the same or have the same effect are each labeled with the same reference numerals in the figures. The figures show schematic diagrams of the invention and form nonspecific parameters of the invention. In addition, the figures show only typical embodiments of the invention and should not restrict the invention to the embodiments depicted here.

Figure 1B:
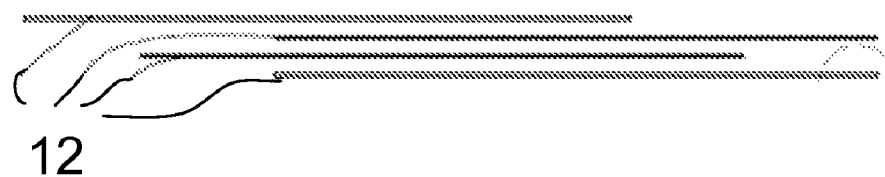

To illustrate the invention, FIG. 1a shows a preferred fiber strand 10 which may form the starting material for a preferred implantable supporting body 100 (FIG. 5) for example. The fiber strand 10 in this example is formed by a plurality of individual fibers 12, as emphasized in FIG. 1b.

Figure 1C:
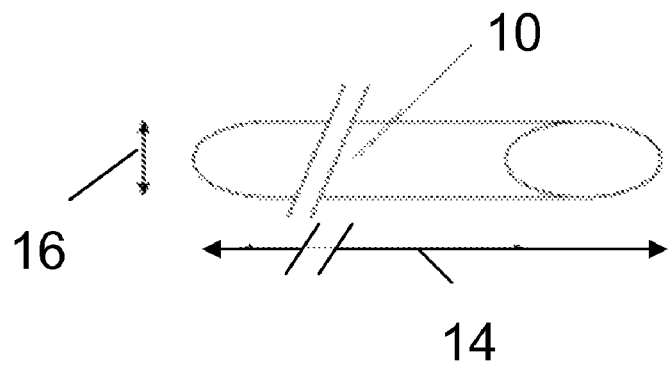

The individual fibers 12 are each much shorter in length than the fiber structure longitudinal extent 14 and are much thinner in their diameter than the fiber structure transverse extent 16, even in the case of an out-of-round cross section of the fiber structure 10 (FIG. 1c). The individual fibers 12 are preferably thinner than the width and thickness of the fiber strand 10. The ratio of longitudinal extent of the individual fiber to fiber strand longitudinal extent 14 is advantageously in the range between 2:1 and 200,000:1, preferably between 10:1 and 100,000:1, and the ratio of the individual fiber transverse extent to the fiber strand transverse extent 16 is in the range between 2:1 and 200,000:1, preferably between 10:1 and 100,000:1.

The individual fibers 12 may be formed from a first group comprising at least one member from the group of carbon or carbonaceous material and/or from metallic materials and/or ceramic materials in pure form, mixed form and in crystalline, partially crystalline or amorphous form. In particular, at least one of the individual fibers 12 may be formed from a metallic material comprising at least one member/element from the second group Fe, Cr, Co, Wo, Ni, Zn, Mg, Ti, Mn, Pt, Mo, Ta, Ir, Ag, Au; or at least one of the individual fibers 12 may be formed from at least one ceramic material comprising at least one member/element from the third group Br, I, Zr, Al, N, F, Si, Ga, Ti, O, Au, Ag. Blends of individual fibers 12 from two or more of the three groups mentioned above are also conceivable.

The individual fibers 12 in the fiber strand 10 may be impregnated with a matrix material 22. The matrix material may be, for example, a substance from the group of drugs, polymers, drug-loaded polymers, drug-loaded biodegradable polymers. The polymer may be formed by at least one monomer from the group of lactides, glycolides, paradioxanones, caprolactone, trimethylene carbonate, mixtures thereof, copolymers thereof. If the matrix material 22 is loaded with a drug, then rapid or slow release of the drug at the site of use can be achieved, depending on the selected polymer. In particular, preferred polymers for the polymer matrix of the inventive implant may be selected from the following groups:

nonresorbable/permanent polymers:
polypropylene, polyethylene, polyvinyl chloride, polymethyl methacrylate, polymethyl methacrylate, polytetra-fluoroethylene, polyvinyl alcohol, polyurethane, poly-butylene terephthalate, silicones, polyphosphazene, as well as their copolymers and blends;

resorbable/bioresorbable/degradable polymers:
polydioxanone, polyglycolide, polycaprolactone, polylactide (poly-L-lactide, poly-D,L-lactide and copolymers and blends, such as poly(L-lactide-co-glycolide), poly(D,L-lactide-co-glycolide), poly(L-lactide-co-D,L-lactide), poly(L-lactide-co-trimethylene carbonate, triblock copoly-mers), polysaccharides (chitosan, levan, hyaluronic acid, heparin, dextran, cellulose, etc.), polyhydroxyvalerate, ethylvinyl acetate, polyethylene oxide, polyphosphorylcholine, fibrin, albumin.

Figure 2A:
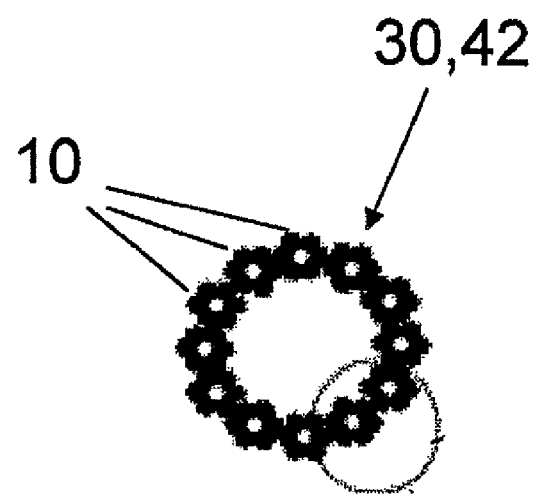
FIGS. 2a, b show a cross section through a preferred fiber body in the form of a tube (FIG. 2a) formed from the cord and fiber strands and a detail of the tube (FIG. 2b).

In an advantageous embodiment of the individual fibers 12, these individual fibers 12 may consist of carbon compounds or oxide compounds, e.g., titanium oxide with diameters in the range of 0.05 μm to 500 μm, preferably around 1 μm. A fiber strand 10 may be braided from the individual fibers 12 and then used to create a fiber body, e.g., in the form of a fiber cord 30, which may be formed as tubes 42. This is illustrated in FIG. 2a as an example as a cross section through the tubes 42. The individual fibers 12 may optionally also be joined together directly to form the tubes 42.

Figure 2B:
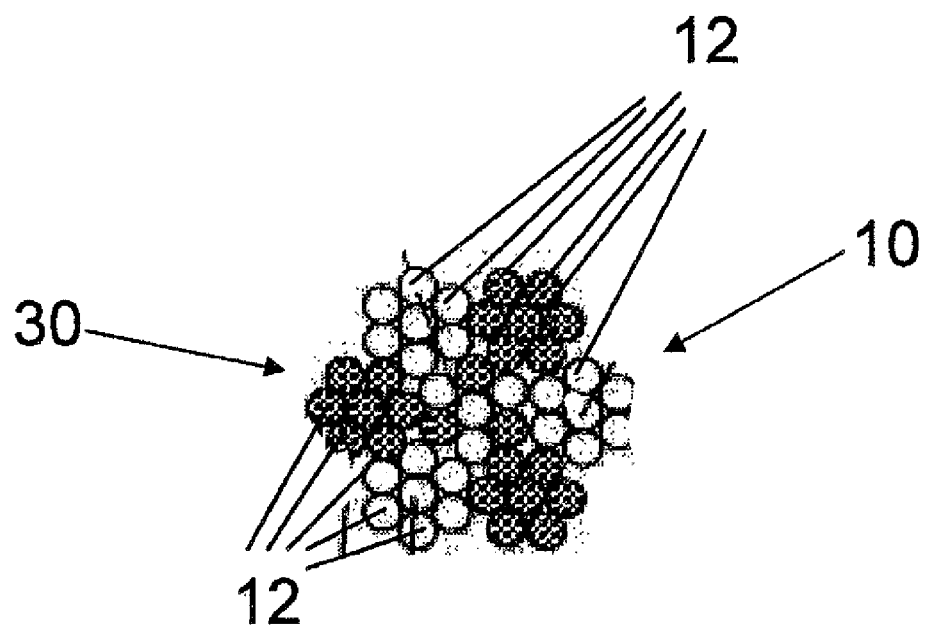

FIG. 2b shows a detail of the sheathing of the tubes 42. The sheathing of the tubes 42 may be formed from cord 30 (unpatterned cross sections) and from individual fibers 12 (patterned cross sections). The tubes 42 may serve as a supporting body of a stent, for example, and may be compressed to a smaller diameter for insertion at the intended site. Only at the target site are the final mechanical property and shape established by an expansion process. The supporting body may be a partial piece of the tube 42 with a length 18 (FIG. 5), which is cut from the tube 42, e.g., by laser cutting. The tube 42 may be impregnated with a polymer, e.g., a PLGA (PLGA=polylactic-co-glycolic acid)) which contains a drug, e.g., has an anti-inflammatory and/or antiproliferative effect.

FIGS. 3a to 3d show advantageous embodiments of a preferred cord 30 (FIG. 3a) in which a sheath 36 comprising one or more fiber strands 10 is arranged around a core 34 (FIGS. 3c, 3d). The core 34 may itself consist of one or more fiber strands 10 (FIG. 3d) and the sheath 36 may be made of a material having at least one core 34 enclosed by a sheath 36. One or more fiber strands 10 may be surrounded by a matrix material 22 (FIG. 3b).

Figure 4B:
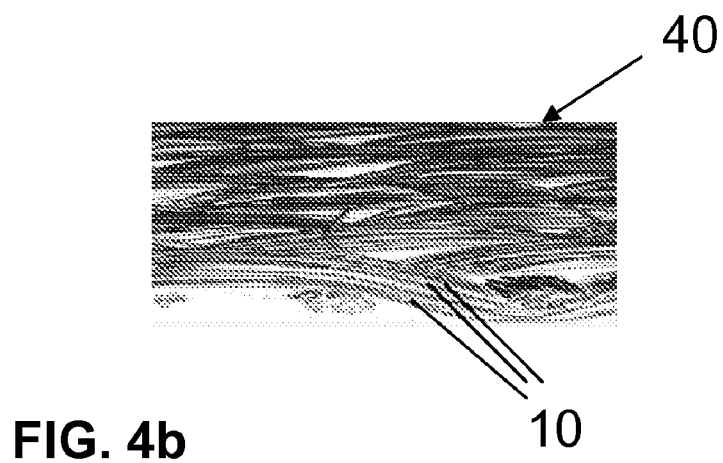
FIGS. 4a, b show a detail of a fiber body (FIG. 4a) in the form of fiber strands and a detail of the fiber body (FIG. 4b).
Figure 4A:
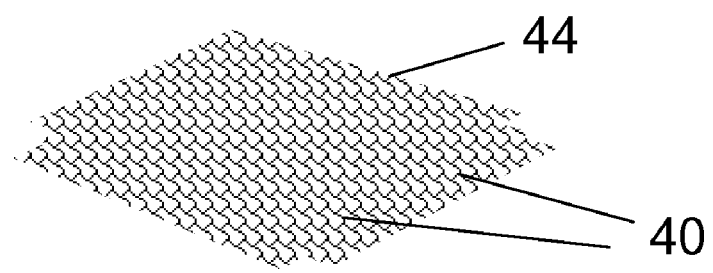

FIGS. 4a and 4b show an advantageous embodiment of a flat fiber body in the form of a sheeting 44 comprising a plurality of fiber strands 10. One or more ribbons 40 having the desired dimensions may be cut out of such sheeting 44 to form a supporting body 100 (FIG. 5), for example, which is then converted to the desired geometry. Such sheeting 44 may also be formed directly from individual fibers 12.

Figure 5:
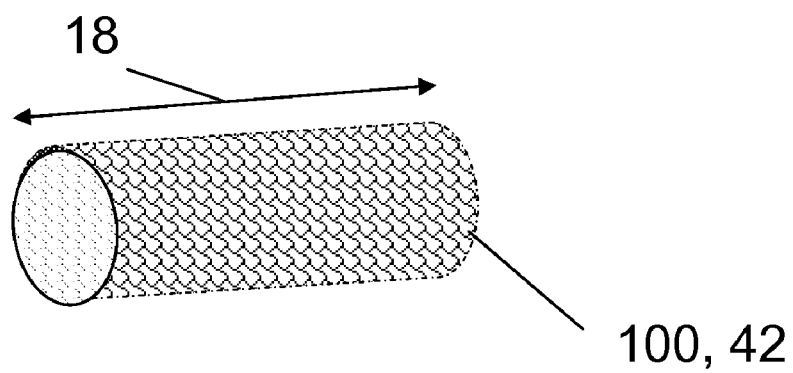
FIG. 5 shows a preferred supporting body of a preferred fiber strand.

A preferred supporting body 100 is illustrated as tube 42 in FIG. 5. The tube 42 is cut to size from a plurality of ribbons 40 from the mat 44, for example, and has been knitted to the desired length and desired diameter. It is also conceivable for sheeting 44 to be shaped directly to form the desired supporting body 100. A cord as illustrated in FIGS. 3a-3e may of course also be processed to form a supporting body 100. The shape, stability and drug loading of the supporting body 100 may advantageously be tailored to the intended purpose provided for the supporting body 100.

If necessary, the supporting body 100 thereby formed may be treated with a drug-loaded polymer, e.g., by impregnation. In comparison with the length 18 of the supporting body 100, the individual fiber lengths 16 (FIG. 1c) are much shorter, and in comparison with the transverse dimensions, the transverse dimensions, e.g., diameter of the individual fibers 12, are considerably thinner than the diameter of the supporting body 100.

What is claimed is:

1. An implantable supporting body (100) comprising at least two fiber strands (10), each comprising at least two individual fibers (12), characterized in that the at least two individual fibers (12) are each shorter in their longitudinal extent than the longitudinal extent (14) of the fiber strand (10) and their transverse extent is thinner than the transverse extent (16) of the fiber strand (10), further characterized in that at least one fiber strand (10) comprises a different fiber material than another fiber strand (10).

2. The implantable supporting body (100) according to claim 1, characterized in that,
at least one of the individual fibers (12) comprises carbon or a carbonaceous material; or
at least one of the individual fibers (12) is made of a metallic material comprising at least one member selected from the group consisting of Fe, Cr, Co, Wo, Ni, Zn, Mg, Ti, Mn, Pt, Mo, Ta, Ir, Ag, and Au in crystalline, partially crystalline or amorphous structure; or
at least one of the individual fibers (12) is made of at least one ceramic material comprising at least one member selected from the group consisting of Br, I, Zr, Al, N, F, Si, Ga, Ti, O, Au and Ag in crystalline, partially crystalline or amorphous structure.

3. The implantable supporting body (100) according to claim 1, characterized in that the individual fibers (12) are treated with a matrix material (22).

4. A fiber strand (10) for an implantable supporting body (100), comprising at least two individual fibers (12), characterized in that,
the at least two individual fibers (12) are each shorter in their longitudinal extent than the longitudinal extent (14) of the fiber strand (10) and their transverse extent is thinner than the transverse extent (16) of the fiber strand (10), further wherein the fiber strand (10) comprises two or more regions along a longitudinal extent that differ in a mechanical property selected from the group consisting of flexibility, mechanical strength, elasticity and rigidity; and
the individual fibers (12) are treated with a matrix material (22) comprising at least one substance selected from the group consisting of a lipid regulator, an immunosuppressant, a vasodilator, a calcium channel blocker, a calcineurin inhibitor, an antiphlogistics, an anti-inflammatory, an anti-allergic, an oligonucleotide, an estrogen, an endothelializing agent, a steroid, a protein or peptide, a proliferation inhibitor, an analgesic, an antirheumatic, paclitaxel, rapamycin,
optionally characterized in that the matrix material is loaded with a member selected from the group consisting of a polymer, a nonresorbable/permanent polymer, polytetrafluoroethylene, a poly-amide, a polyether imide, polyether sulfone, poly(iso)butylene, polyvinyl chloride, polyvinyl fluoride, polyvinyl alcohol, polyurethane, polybutylene terephthalate, a silicone, polyphosphazene, or a polymer foam,
optionally further characterized in that the polymer is loaded with a member selected from the group consisting of a resorbable/bioresorbable/degradable polymer, copolymer or a blend, a triblock copolymer, a polysaccharide, polyhydroxy valerate, ethylvinyl acetate, polyethylene oxide, polyphos-phorylcholine, fibrin, albumin, and polyhydroxybutyric acid.

5. The fiber strand (10) according to claim 4, characterized in that the lipid regulator is a fibrate; the vasodilator is a sartan; the calcineurin inhibitor is tacrolimus; the antiphlogistic is cortisone or diclofenac; the anti-inflammatory is imidazole; the oligonucleotide is dODN; the estrogen is genistein; the endothelializing agent is fibrin; the nonresorbable/permanent polymer is selected from the group consisting of polypropylene, polyethylene, polyvinyl chloride, and polyacrylate, wherein the polyacrylate is selected from the group consisting of polyethyl or polymethyl acrylate, polymethyl methacrylate, polymethyl-co-ethyl-acrylate, and ethylene/ethyl acrylate; the polytetrafluoroethylene is ethylene/chlorotrifluoroethylene copolymer; the poly-amide is selected from the group consisting of polyamide imide, PA-11, PA-12, PA46, or PA-66; the polymer foams is from a carbonate or styrene; the polymer loaded with resorbable/bioresorbable/degradable polymer is selected from the group consisting of polydioxanone, polyglycolide, polycaprolactone, polylactide, poly-L-lactide, poly-D,L-lactide; the copolymer or blend is selected from the group consisting of poly(L-lactide-co-glycolide), poly(D,L-lactide-co-glycolide), poly(L-lactide-co-D,L-lactide), poly(L-lactide-co-trimethylene carbonate); the polysaccharide is selected from the group consisting of chitosan, levan, hyaluronic acid, heparin, dextran, and cellulose; and the polyhydroxybutyric acid is selected from the group consisting of atactic, isotactic, syndiotactic, and a blend thereof.

6. The fiber strand (10) according to claim 4, characterized in that the polymer is formed from at least one monomer selected from the group consisting of a lactide, a glycolide, a paradioxanone, a caprolactone, trimethylene carbonate, caprolactone, and a mixture thereof or a copolymer thereof.

7. The implantable supporting body (100) according to claim 1, characterized in that the individual fibers (12) or at least parts of at least one fiber strand (10) are degradable or resorbable.

8. The implantable supporting body (100) according to claim 1, wherein the implantable supporting body (100) comprises a member selected from the group consisting of a cord (30), a ribbon (40), a tube (42), and a mat (44).

9. An implantable supporting body (100) of at least two fiber strands (10), the at least two fiber strands (10) each comprising at least two individual fibers (12), characterized in that the at least two individual fibers (12) are each shorter in their longitudinal extent than the longitudinal extent (14) of the fiber strand (10) and their transverse extent is thinner than the transverse extent (16) of the fiber strand (10), further wherein the fiber strand (10) comprises two or more regions along a longitudinal extent that differ in a mechanical property selected from the group consisting of flexibility, mechanical strength, elasticity and rigidity.

10. The implantable supporting body (100) according to claim 9, wherein the at least two fiber strands (10) comprise a plurality of fiber strands (10), further wherein the implantable supporting body (100) comprises a core and a sheath each formed by two or more of the plurality of fiber strands (10).

11. An implantable supporting body (100) of at least two cords (30) formed from a plurality of fiber strands (10), wherein each fiber strand (10) comprises at least two individual fibers (12), characterized in that the at least two individual fibers (12) are each shorter in their longitudinal extent than the longitudinal extent (14) of the fiber strand (10) and their transverse extent is thinner than the transverse extent (16) of the fiber strand (10), further wherein the fiber strand (10) comprises two or more regions along a longitudinal extent that differ in a mechanical property selected from the group consisting of flexibility, mechanical strength, elasticity and rigidity.

12. The implantable supporting body (100) according to claim 11, wherein the least two cords (30) surround a core formed by another plurality of fiber strands (10).

13. The implantable supporting body (100) according to claim 3, characterized in that the matrix material (22) comprises at least one substance selected from the group consisting of a lipid regulator, an immunosuppressant, a vasodilator, a calcium channel blocker, a calcineurin inhibitor, an antiphlogistics, an anti-inflammatory, an anti-allergic, an oligonucleotide, an estrogen, an endothelializing agent, a steroid, a protein or peptide, a proliferation inhibitor, an analgesic, an antirheumatic, paclitaxel, rapamycin,
 optionally characterized in that the matrix material is loaded with a member selected from the group consisting of a polymer, a nonresorbable/permanent polymer, polytetrafluoroethylene, a poly-amide, a polyether imide, polyether sulfone, poly(iso)butylene, polyvinyl chloride, polyvinyl fluoride, polyvinyl alcohol, polyurethane, polybutylene terephthalate, a silicone, polyphosphazene, or a polymer foam,
 optionally further characterized in that the polymer is loaded with a member selected from the group consisting of a resorbable/bioresorbable/degradable polymer, copolymer or a blend, a triblock copolymer, a polysaccharide, polyhydroxy valerate, ethylvinyl acetate, polyethylene oxide, polyphos-phorylcholine, fibrin, albumin, and polyhydroxybutyric acid.

14. The implantable supporting body (100) according to claim 4, characterized in that the individual fibers (12) are degradable or resorbable.

15. The implantable supporting body (100) according to claim 9, characterized in that at least one fiber strand (10) is treated with a matrix material (22).

16. The implantable supporting body (100) according to 15, characterized in that the matrix material (22) comprises at least one substance selected from the group consisting of a lipid regulator, an immunosuppressant, a vasodilator, a calcium channel blocker, a calcineurin inhibitor, an antiphlogistics, an anti-inflammatory, an anti-allergic, an oligonucleotide, an estrogen, an endothelializing agent, a steroid, a protein or peptide, a proliferation inhibitor, an analgesic, an antirheumatic, paclitaxel, rapamycin,
 optionally characterized in that the matrix material is loaded with a member selected from the group consisting of a polymer, a nonresorbable/permanent polymer, polytetrafluoroethylene, a poly-amide, a polyether imide, polyether sulfone, poly(iso)butylene, polyvinyl chloride, polyvinyl fluoride, polyvinyl alcohol, polyurethane, polybutylene terephthalate, a silicone, polyphosphazene, or a polymer foam,
 optionally further characterized in that the polymer is loaded with a member selected from the group consisting of a resorbable/bioresorbable/degradable polymer, copolymer or a blend, a triblock copolymer, a polysaccharide, polyhydroxy valerate, ethylvinyl acetate, polyethylene oxide, polyphos-phorylcholine, fibrin, albumin, and polyhydroxybutyric acid.

17. The implantable supporting body (100) according to claim 9, characterized in that the individual fibers (12) are degradable or resorbable.

18. An implantable supporting body (100) comprising at least two fiber strands (10), each comprising at least two individual fibers (12), characterized in that the at least two individual fibers (12) are each shorter in their longitudinal extent than the longitudinal extent (14) of the fiber strand (10) and their transverse extent is thinner than the transverse extent (16) of the fiber strand (10), further characterized in that,
 at least one of the individual fibers (12) is made of a metallic material comprising at least one member selected from the group consisting of Fe, Cr, Co, Wo, Ni, Zn, Mg, Ti, Mn, Pt, Mo, Ta, Ir, Ag, and Au in crystalline, partially crystalline or amorphous structure; or
 at least one of the individual fibers (12) is made of at least one ceramic material comprising at least one member selected from the group consisting of Br, I, Zr, Al, N, F, Si, Ga, Ti, O, Au and Ag in crystalline, partially crystalline or amorphous structure.

19. The implantable supporting body (100) according to claim 18, characterized in that at least one fiber strand (10) is treated with a matrix material (22).

20. The implantable supporting body (100) according to claim 19, characterized in that the matrix material (22) comprises at least one substance selected from the group consisting of a lipid regulator, an immunosuppressant, a vasodilator, a calcium channel blocker, a calcineurin inhibitor, an antiphlogistics, an anti-inflammatory, an anti-allergic, an oligonucleotide, an estrogen, an endothelializing agent, a steroid, a protein or peptide, a proliferation inhibitor, an analgesic, an antirheumatic, paclitaxel, rapamycin,
 optionally characterized in that the matrix material is loaded with a member selected from the group consisting of a polymer, a nonresorbable/permanent polymer, polytetrafluoroethylene, a poly-amide, a polyether imide, polyether sulfone, poly(iso)butylene, polyvinyl chloride, polyvinyl fluoride, polyvinyl alcohol, polyurethane, polybutylene terephthalate, a silicone, polyphosphazene, or a polymer foam, optionally further characterized in that the polymer is loaded with a member selected from the group consisting of a resorbable/bioresorbable/degradable polymer, copolymer or a blend, a triblock copolymer, a polysaccharide, polyhydroxy valerate, ethylvinyl acetate, polyethylene oxide, polyphos-phorylcholine, fibrin, albumin, and polyhydroxybutyric acid.

* * * * *